(12) United States Patent
Casar et al.

(10) Patent No.: US 9,376,397 B2
(45) Date of Patent: Jun. 28, 2016

(54) KEY INTERMEDIATES FOR THE SYNTHESIS OF ROSUVASTATIN OR PHARMACEUTICALLY ACCEPTABLE SALTS THEREOF

(71) Applicant: LEK PHARMACEUTICALS D.D., Ljubljana (SI)

(72) Inventors: Zdenko Casar, Ljubljana (SI); Janez Kosmrlj, Ljubljana (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 0 days.

(21) Appl. No.: 14/609,248

(22) Filed: Jan. 29, 2015

(65) Prior Publication Data

US 2015/0141449 A1    May 21, 2015

Related U.S. Application Data

(62) Division of application No. 13/145,783, filed as application No. PCT/EP2010/051163 on Feb. 1, 2010, now abandoned.

(30) Foreign Application Priority Data

Feb. 2, 2009    (EP) .................................. 09151881

(51) Int. Cl.
| | |
|---|---|
| C07D 239/42 | (2006.01) |
| C07D 405/06 | (2006.01) |
| C07F 9/54 | (2006.01) |
| C07F 9/535 | (2006.01) |
| A61K 31/505 | (2006.01) |
| A61K 31/506 | (2006.01) |

(52) U.S. Cl.
CPC ............ *C07D 239/42* (2013.01); *A61K 31/505* (2013.01); *A61K 31/506* (2013.01); *C07D 405/06* (2013.01); *C07F 9/535* (2013.01); *C07F 9/54* (2013.01)

(58) Field of Classification Search
CPC .. C07D 239/42; C07D 405/06; C07F 7/1856; C07F 9/54; C07F 9/535
USPC ........................................................ 544/322
See application file for complete search history.

(56) References Cited

U.S. PATENT DOCUMENTS

| | | |
|---|---|---|
| 8,183,397 B2 | 5/2012 | Casar et al. |
| 8,269,001 B2 | 9/2012 | Casar |
| 2005/0124639 A1 | 6/2005 | Joshi et al. |

FOREIGN PATENT DOCUMENTS

EP            1775299 A1     4/2007

OTHER PUBLICATIONS

Xiao-Li Zhou et al., "N-[4-(4-Fluorophenyl)-5-methyl-6-isopropyl-pyrimidin-2-yl]-N-methylmethanesulfonamide", Acta Cryst., vol. E63, 2007, (XP002527601) pp. 01293-01294.

*Primary Examiner* — Venkataraman Balasubramanian
(74) *Attorney, Agent, or Firm* — Arent Fox LLP

(57) ABSTRACT

The present invention relates in general to the field of organic chemistry and in particular to the preparation of N-(4-(4-fluorophenyl)-6-isopropyl-5-methylpyrimidin-2-yl)-N-methylmethanesulfonamide (I), N-(4-(4-fluorophenyl)-5-(bromomethyl)-6-isopropylpyrimidin-2-yl)-N-methylmethanesulfonamide (II) and N-(4-(4-fluorophenyl)-5-(hydroxymethyl)-6-isopropylpyrimidin-2-yl)-N-methylmethanesulfonamide (III), key intermediates in preparation of Rosuvastatin.

18 Claims, No Drawings

KEY INTERMEDIATES FOR THE SYNTHESIS OF ROSUVASTATIN OR PHARMACEUTICALLY ACCEPTABLE SALTS THEREOF

CROSS-REFERENCE TO RELATED APPLICATIONS

This application is a divisional of U.S. patent application Ser. No. 13/145,783, filed Oct. 3, 2011, which is a 371 National Stage entry of International Application No. PCT/EP2010/051163, filed Feb. 1, 2010, which claims the benefit of priority from European Application No. 09151881.1, filed Feb. 2, 2009. The entire contents of these applications are incorporated herein by reference.

FIELD OF THE INVENTION

The present invention relates to a process for the preparation of N-(4-(4-fluorophenyl)-5-(bromomethyl)-6-isopropylpyrimidin-2-yl)-N-methylmethanesulfonamide, N-(4-(4-fluorophenyl)-5-(hydroxymethyl)-6-isopropylpyrimidin-2-yl)-N-methylmethanesulfonamide and N-(4-(4-fluorophenyl)-6-isopropyl-5-methylpyrimidin-2-yl)-N-methylmethanesulfonamide, useful as key intermediates for the preparation of Rosuvastatin or pharmaceutically acceptable salts thereof. The present invention further relates to a process wherein the above mentioned compounds are used as intermediates.

BACKGROUND OF THE INVENTION (N-(4-(4-fluorophenyl)-5-(bromomethyl)-6-isopropylpyrimidin-2-yl)-N-methylmethanesulfonamide), (N-(4-(4-fluorophenyl)-5-(hydroxymethyl)-6-isopropylpyrimidin-2-yl)-N-methylmethanesulfonamide) and N-(4-(4-fluorophenyl)-6-isopropyl-5-methylpyrimidin-2-yl)-N-methylmethanesulfonamide are possible intermediates in the synthesis of Rosuvastatin and its pharmaceutically acceptable salts. Rosuvastatin calcium, chemically described as bis [(E)-7-[4-(4-fluorophenyl)-6-isopropyl-2-[methyl(methylsulfonyl)amino]pyrimidin-5-yl] (3R,5S)-3,5-dihydroxyhept-6-enoic acid] calcium salt, is a synthetic lipid-lowering agent that acts as an inhibitor of 3-hydroxy-3-methylglutaryl-coenzyme A (HMG-CoA) reductase (HMG-CoA Reductase inhibitor). HMG-CoA reductase inhibitors are commonly referred to as "statins." Statins are therapeutically effective drugs used for reducing low density lipoprotein (LDL) particle concentration in the blood stream of patients at risk for cardiovascular disease. Therefore, Rosuvastatin calcium is used in the treatment of hypercholesterolemia and mixed dyslipidemia.

The EP 521471 A1 discloses Rosuvastatin and a process for its preparation, among others by a process comprising a step of preparing N-(4-(4-fluorophenyl)-5-(hydroxymethyl)-6-isopropylpyrimidin-2-yl)-N-methylmethanesulfonamide by reduction of a suitable ester derivative thereof with diisobutylaluminium hydride (DIBAL-H) as a reduction reagent. Furthermore, WO2008/059519 A2 also describes the preparation of Rosuvastatin via N-(4-(4-fluorophenyl)-5-(hydroxymethyl)-6-isopropylpyrimidin-2-yl)-N-methylmethanesulfonamide as intermediate obtained by reduction of a suitable ester thereof by means of DIBAL-H.

International patent application WO2007/017117 A1 describes the preparation of Rosuvastatin via N-(4-(4-fluorophenyl)-5-(bromomethyl)-6-isopropylpyrimidin-2-yl)-N-methylmethanesulfonamide as the intermediate. This intermediate is prepared by nucleophilic substitution of N-(4-(4-fluorophenyl)-5-(hydroxymethyl)-6-isopropylpyrimidin-2-yl)-N-methylmethanesulfonamide by means of HBr as the source of nucleophile.

The object of the present invention is to provide an improved process for preparing N-(4-(4-fluorophenyl)-5-(bromomethyl)-6-isopropylpyrimidin-2-yl)-N-methylmethanesulfonamide, N-(4-(4-fluorophenyl)-5-(hydroxymethyl)-6-isopropylpyrimidin-2-yl)-N-methylmethanesulfonamide and N-(4-(4-fluorophenyl)-6-isopropyl-5-methylpyrimidin-2-yl)-N-methylmethanesulfonamide, so as to provide valuable intermediates for the preparation of Rosuvastatin and pharmaceutically acceptable salts thereof.

SUMMARY OF THE INVENTION

The object is solved by processes for the preparation of N-(4-(4-fluorophenyl)-5-(bromomethyl)-6-isopropylpyrimidin-2-yl)-N-methylmethanesulfonamide, N-(4-(4-fluorophenyl)-5-(hydroxymethyl)-6-isopropylpyrimidin-2-yl)-N-methylmethanesulfonamide and N-(4-(4-fluorophenyl)-6-isopropyl-5-methylpyrimidin-2-yl)-N-methylmethanesulfonamide according to claims 1, 9, 13 and 15, a process for the preparation of Rosuvastatin or pharmaceutically acceptable salts thereof according to claims 11 and 17, a preparation of a pharmaceutical composition according to claims 18 and 19 and a use of N-(4-(4-fluorophenyl)-5-(bromomethyl)-6-isopropylpyrimidin-2-yl)-N-methylmethanesulfonamide, N-(4-(4-fluorophenyl)-5-(hydroxymethyl)-6-isopropylpyrimidin-2-yl)-N-methylmethanesulfonamide and N-(4-(4-fluorophenyl)-6-isopropyl-5-methylpyrimidin-2-yl)-N-methylmethanesulfonamide for the preparation of Rosuvastatin or pharmaceutically acceptable salts thereof according to claim 20 respectively. Preferred embodiments are set forth below and in the subclaims.

According to the present invention, it has been surprisingly found that a more efficient and easier to handle synthesis of N-(4-(4-fluorophenyl)-5-(bromomethyl)-6-isopropylpyrimidin-2-yl)-N-methylmethanesulfonamide and N-(4-(4-fluorophenyl)-5-(hydroxymethyl)-6-isopropylpyrimidin-2-yl)-N-methylmethanesulfonamide respectively can be carried out by selecting suitable starting materials which can be converted to the desired product without the necessity of aggressive, difficult to handle and/or expensive reagents. Moreover, the process for the preparation is more efficient as it allows beneficial reaction conditions providing for less by products and thus higher purity of the products and higher yields, and/or less necessary reaction steps. Furthermore, the process according to the present invention enables to use mild reactants, further contributing to an easier handling in terms of less necessary precautions concerning application and storage, and less precautions concerning the requirement of special reaction conditions such as protective gas atmosphere and/or anhydrous solvent. Furthermore an efficient process for recovering of N-(4-(4-fluorophenyl)-6-isopropyl-5-methylpyrimidin-2-yl)-N-methylmethanesulfonamide is disclosed that has an favorable impact on the efficiency of the overall process of the rosuvastatin synthesis. As a result, desirable key intermediates for the preparation of Rosuvastatin or pharmaceutically acceptable salts thereof are provided by a significantly improved process.

Various aspects, advantageous features and preferred embodiments of the present invention, which respectively alone and in combination particularly contribute to solving the object of the invention are summarized in the following items:

(1) A process for preparing the compound of formula II

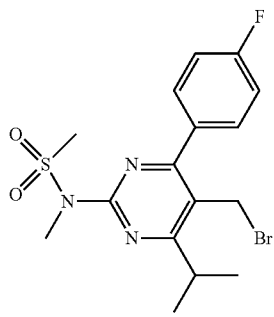

comprising the steps of:
providing a compound of formula I:

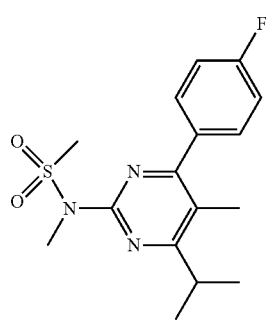

and converting the compound of formula I by bromination into the compound of formula II.

(2) The process according to item (1), wherein bromination proceeds by radical reaction (3) The process according to item (1) or (2), wherein said bromination is performed with an N-bromoamide as a brominating agent, preferably an N-bromoamide selected from the group consisting of N-bromoacetamide, N,N-dibromobenzene sulfonamides, N-bromosuccinimide, N-bromophthalimide, N-bromoglutarimide, 3-bromo-hydantoin and 1,3-dibromo-5,5-dimethylhydantoin, more preferably N-bromosuccinimide.

(4) The process according to item (3), wherein the initial amount of brominating agent is from about 1 to about 3 times the molar stoichiometric amount based on compound I, preferably about 1.2 to about 2.5 times, more preferably about 1.4 to about 2.2 times, and in particular about 2 times.

(5) The process according to any one of items (1) to (4) avoiding use of HBr and PBr$_3$.

(6) The process according to any one of the preceding items, wherein the bromination reaction is performed in an organic solvent selected from the group consisting of acetone, ethyl acetate, hydrocarbons, aromatic hydrocarbons and acetonitrile or a mixture thereof, preferably the organic solvent is acetonitrile.

(7) The process according to items (1) to (6), wherein the bromination is performed under a treatment of ultraviolet radiation.

(8) The process according to item (7), wherein said ultraviolet radiation has a wavelength of about 200-400 nm, preferably about 310 nm.

(9) The process according to item (7) or (8), wherein said ultraviolet radiation is performed for 2 to 10 hours, preferably for about 4 hours.

(10) The process according to any one of items (1) to (9), wherein the bromination is carried out at a temperature between 0 to 90° C., preferably between 10 to 65° C., more preferably between 15 to 35° C. and in particular between 19 to 25° C.

(11) The process according to any one of the preceding items, wherein no radical former is applied.

(12) The process according to any one of items (1) to (10), wherein a radical former is applied, wherein the radical former is preferably an organic peroxide, an organic peracid, an organic hydroperoxide or an organic azo compound, more preferably the radical former is benzoyl peroxide or azoisobutyronitrile.

(13) The process according to item (12), wherein the initial amount of radical former is between about 0 to 0.5 molar stoichiometric amount based on compound I, preferably about 0 to 0.07 molar stoichiometric amount based on compound I, and more preferably no radical former is applied.

(14) The process according to any one of the preceding items, further comprising a step of purifying of the compound of formula II, preferably by crystallization.

(15) The process according to item (14), wherein crystallisation is performed with an MTBE/hexane mixture, preferably with an MTBE/hexane mixture, wherein the volume ratio of MTBE to hexane is 2 to 1, preferably 1 to 1 and more preferably 2 to 3.

(16) A process for preparing a compound of formula I

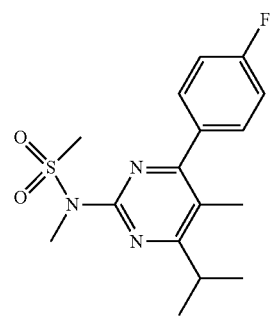

comprising a step of reacting a compound of formula IX or IX'

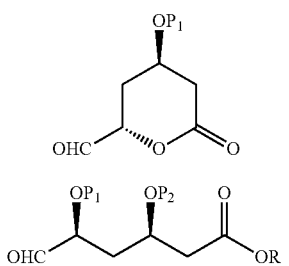

wherein P$_1$ and P$_2$ respectively denote same or different hydroxy protecting groups and R is selected from alkyl or aryl;

with a compound of formula X or X'

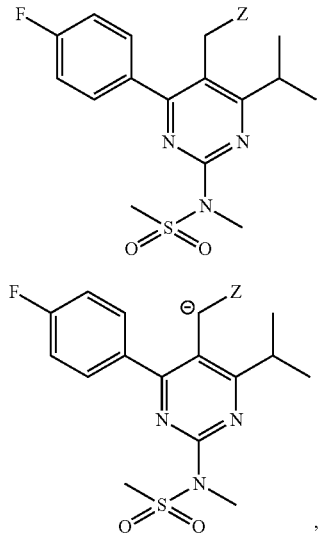

wherein Z is selected from the group consisting of:

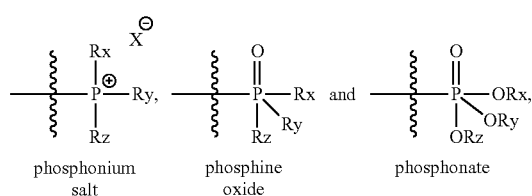

and wherein Rx, Ry, and Rz, are the same or different and are selected from optionally substituted C$_1$-C$_8$ alkyl or C$_3$-C$_6$ cycloalkyl or C$_1$-C$_8$ alkenyl or C$_5$-C$_6$ cycloalkenyl or aryl, preferably phenyl, and X$^\ominus$ is an anion, preferably a halogen or carboxylate anion, more preferably chloride, bromide or trifluoroacetate;

wherein in said reaction the compound of formula X or X' is used in molar excess over the compound of formula IX or IX', and/or wherein the reaction takes place in the presence of water or other protic molecules, to obtain the compound of formula I.

(17) The process according to item (16), wherein the compound of formula I is obtained as a product besides a compound selected from formulas XI or XI'

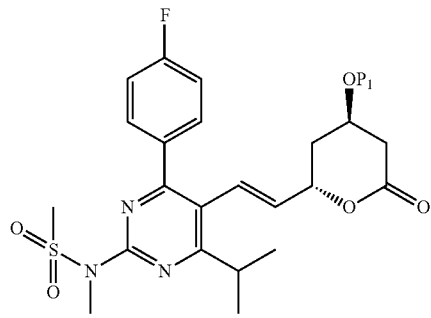

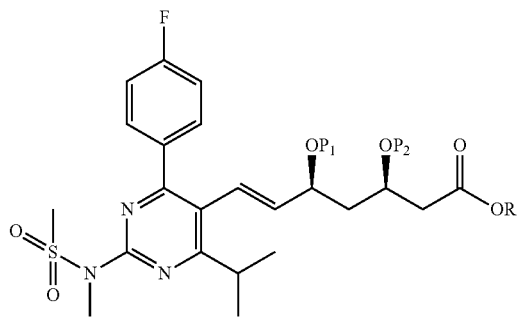

wherein P$_1$ and P$_2$ are as defined above;

wherein said compound selected from formulas XI and XI' is subsequently used for conversion into Rosuvastatin or its salt, and wherein the compound of formula I is used to provide said compound in a process according to claim 1.

In this way, the compound of formula I can be efficiently recycled to perform a further synthesis route for the preparation of Rosuvastatin or its salt.

(18) A process for preparing rosuvastatin, comprising:

(a) reacting a compound of formula IX or IX'

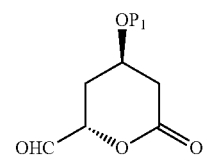

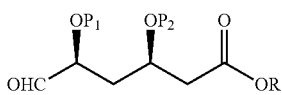

wherein P$_1$ and P$_2$ respectively denote same or different hydroxy protecting groups and R is selected from alkyl or aryl;

with a compound of formula X or X'

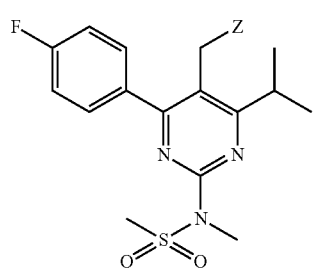

-continued

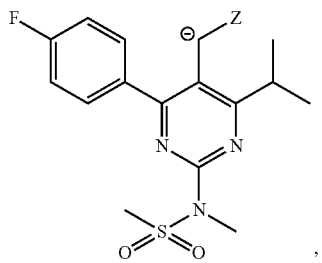

wherein Z is selected from the group consisting of:

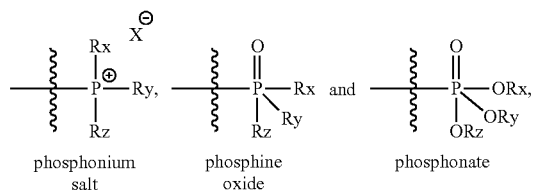

and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, preferably phenyl, and $X^\ominus$ is an anion, preferably a halogen or carboxylate anion, more preferably chloride, bromide or trifluoroacetate;

(b) obtaining reaction products of
a compound of formula I

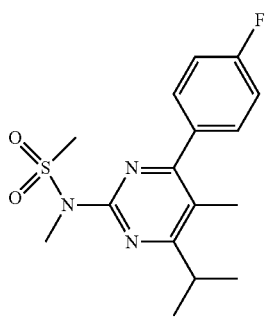

and
a compound selected from formulas XI or XI'

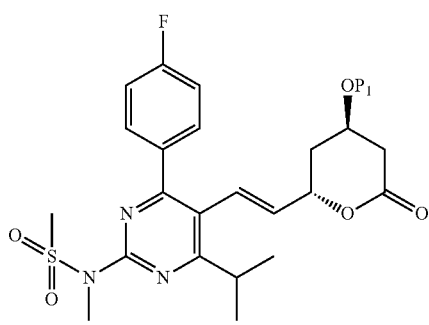

-continued

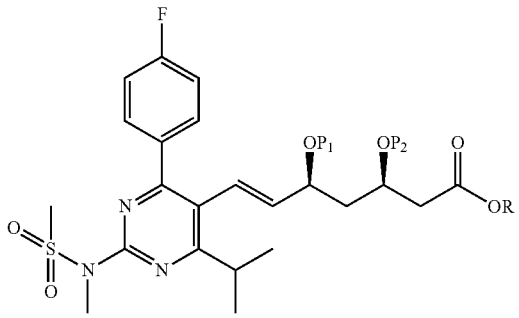

wherein $P_1$ and $P_2$ are as defined above;
(c) using the obtained compound selected from formulas XI and XI' for conversion into Rosuvastatin or its salt; and
(d) using the obtained compound of formula I for providing said compound in a process according to item (1) in a recycling process for producing rosuvastatin.

(19) The process according to item (18), wherein in step (b) the obtained reaction products are respectively separated into the compound of formula I and the compound selected from formulas XI or XI', prior to the respective use in step (d).

In the manner defined by items (18) and (19), an advantageous and generally applicable recycling process is provided for improving the overall yield of Rosuvastatin or its salt.

(20) A process for preparing a compound of formula III,

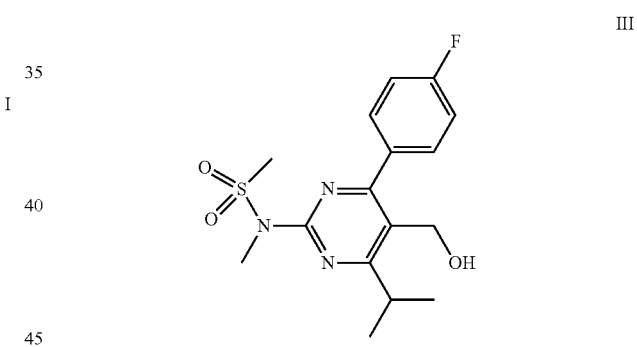

comprising the step of converting the compound of formula II

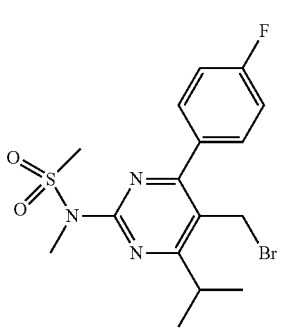

by hydrolysis into the compound of formula III.
(21) The process according to item (20), wherein hydrolysis is performed in the presence of an inorganic base, preferably an alkaline or alkaline earth carbonate or hydrogencarbonate, more preferably NaHCO₃.
(22) The process according to item (21), wherein the inorganic base is added to the reaction mixture in the form of a saturated aqueous solution.
(23) The process according to any one of items (21)-(22), wherein the initial amount of inorganic base is between about 1 to 10 times the molar stoichiometric amount based on compound II, preferably about 3 to 7 and more preferably 5 to 6 times.
(24) A one-pot process for preparing the compound of formula III

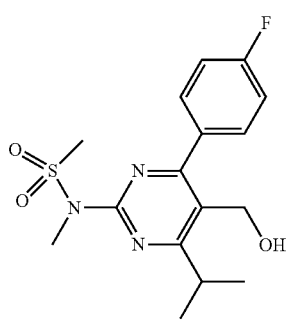

comprising converting compound of formula I

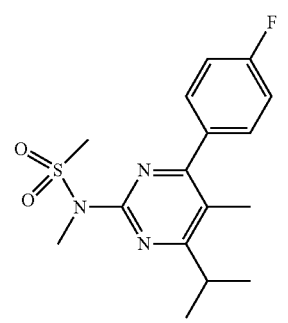

by reaction via non-isolated compound of formula II

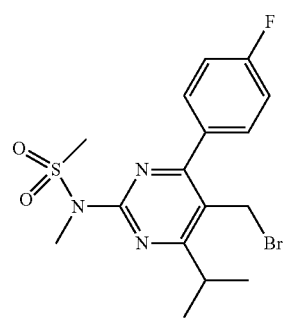

into the compound of formula III.
(25) The process according to item (24), wherein conversion of the compound of formula I into the compound of formula II is carried out by the process of any one of items (1) to (13).

(26) The process according to item (24) or (25), wherein conversion of the compound of formula II into the compound of formula III is carried out by the process of any one of items (20) to (23)
(27) The process according to any one of items (24) to (26), wherein a reaction batch after converting compound of formula I into compound of formula II is diluted with a solvent as defined under item (6).
(28) The process according to any one of items (20) to (27), further comprising the step of purifying compound of formula III, preferably by crystallization.
(29) The process according to item (28), wherein crystallisation is performed with an MTBE/hexane mixture, preferably with an MTBE/hexane mixture wherein the volume ratio of MTBE to hexane is 2 to 1, preferably 1 to 1 and more preferably 2 to 3.
(30) A process for the preparation of Rosuvastatin or pharmaceutically acceptable salt of Rosuvastatin, comprising the steps of:
 a) carrying out a process for preparing the compound of formula I according to item (16), and
 b) subjecting the compound of formula I to further synthesis steps to yield Rosuvastatin or pharmaceutically acceptable salts thereof.
(31) A process for the preparation of Rosuvastatin or pharmaceutically acceptable salt of Rosuvastatin, comprising the steps of:
 a) carrying out a process for preparing the compound of formula II according to any one of items (1) to (15), and
 b) subjecting the compound of formula II to further synthesis steps to yield Rosuvastatin or pharmaceutically acceptable salts thereof.
(32) A process for the preparation of Rosuvastatin or pharmaceutically acceptable salt of Rosuvastatin, comprising the steps of:
 a) carrying out a process for preparing the compound of formula III according to any one of items (20) to (29), and
 b) subjecting the compound of formula III to further synthesis steps to yield Rosuvastatin or pharmaceutically acceptable salts thereof.
(33) A process for the preparation of a pharmaceutical composition comprising Rosuvastatin as active ingredient, comprising the steps of:
 a) preparing Rosuvastatin or pharmaceutically acceptable salts thereof according to the process according to item (31) or (32), and
 b) admixing the thus prepared Rosuvastatin or pharmaceutically acceptable salt thereof with at least one pharmaceutically acceptable excipient.
(34) A process for the preparation of a pharmaceutical composition comprising Rosuvastatin as active ingredient, comprising the steps of:
 a) preparing Rosuvastatin or pharmaceutically acceptable salts thereof according to the process according to any one of items (17) to (19),
 b) admixing the thus prepared Rosuvastatin or pharmaceutically acceptable salt thereof with at least one pharmaceutically acceptable excipient.
(35) Use of compound of formula II prepared according to the process of any one of items (1) to (15) for the preparation of Rosuvastatin or pharmaceutically acceptable salts thereof.
(36) Use of compound of formula III prepared according to the process of any one of items (20) to (29) for the preparation of Rosuvastatin or pharmaceutically acceptable salts thereof.

(37) Use of the compound of formula I prepared according to any one of the processes of items (16) to (19) for the preparation of Rosuvastatin or pharmaceutically acceptable salts thereof.

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

In order to improve a process for the preparation of a compound of formula II (N-(4-(4-fluorophenyl)-5-(bromomethyl)-6-isopropylpyrimidin-2-yl)-N-methylmethanesulfonamide) and a compound of formula III (N-(4-(4-fluorophenyl)-5-(hydroxymethyl)-6-isopropylpyrimidin-2-yl)-N-methylmethanesulfonamide), extensive test series were carried out by the inventors to find critical factors that are particularly suited to increase the product yields and to decrease byproducts, while significantly simplifying preparation due to beneficial reaction conditions and/or less necessary reaction steps.

Conventionally, the compound of formula III was prepared by reduction of a suitable ester derivative of the formula IV (wherein R preferably denotes a methyl or ethyl residue) by means of a suitable reducing agent in a late or last step of a multi step synthesis procedure, as illustrated on the following scheme:

However, this type of reduction has significant procedural drawbacks. Most commonly, reduction is carried out by diisobutylaluminium hydride (DIBAL-H) as the reducing agent, and therefore the reduction must be carried out at temperatures around or below 0° C. (preferably up to −70° C.) under dry/anhydrous conditions. A further drawback of the reduction with DIBAL-H is that the complex hydride DIBAL-H is an expensive and hazardous reagent. Less common, the reduction is carried out with $KBH_4/ZnCl_2$ as the reducing agent, which also requires dry/anhydrous conditions. Moreover, there is the problem of unreacted starting material and generation of byproducts which are hardly removed in the subsequent Rosuvastatin synthesis steps if dry/anhydrous conditions are not employed and reaction does't go to completition.

As shown on the following scheme, conventionally, the compound of formula III was then converted into the compound of formula II by a nucleophilic substitution reaction using HBr or $PBr_3$ in order to introduce bromine:

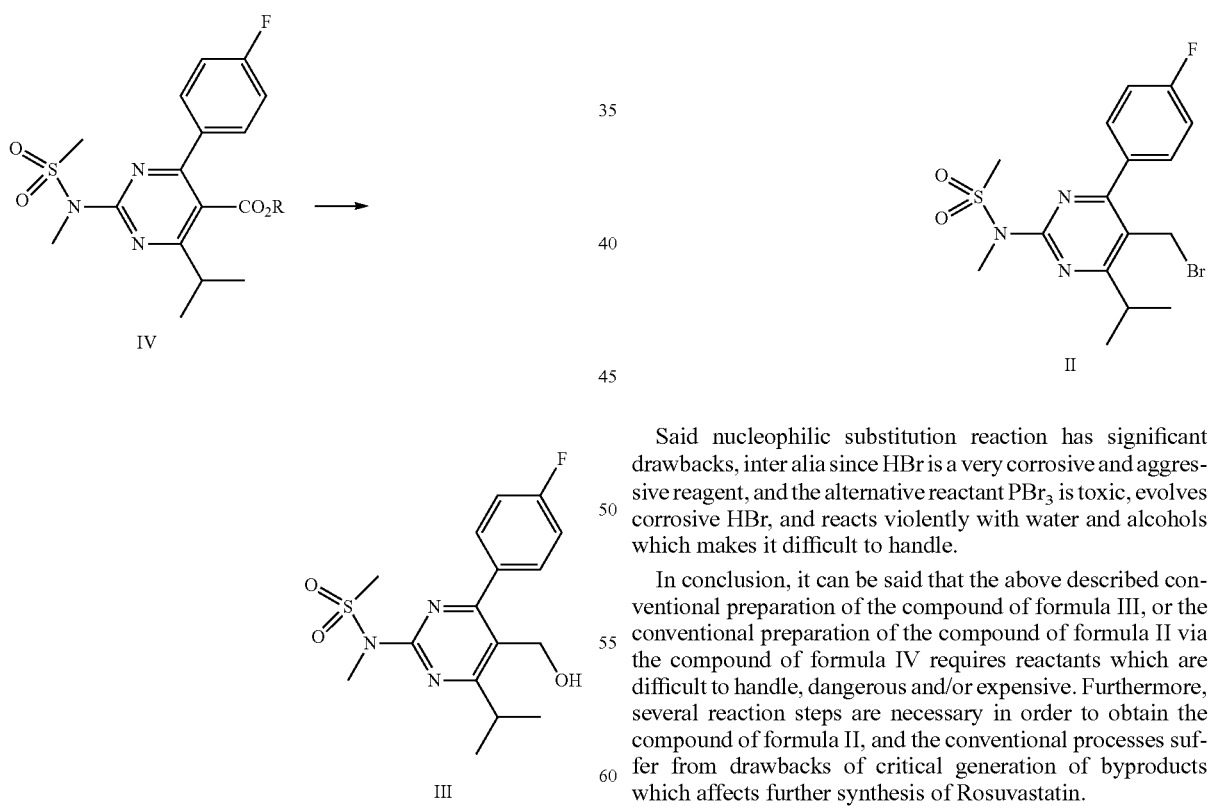

Said nucleophilic substitution reaction has significant drawbacks, inter alia since HBr is a very corrosive and aggressive reagent, and the alternative reactant $PBr_3$ is toxic, evolves corrosive HBr, and reacts violently with water and alcohols which makes it difficult to handle.

In conclusion, it can be said that the above described conventional preparation of the compound of formula III, or the conventional preparation of the compound of formula II via the compound of formula IV requires reactants which are difficult to handle, dangerous and/or expensive. Furthermore, several reaction steps are necessary in order to obtain the compound of formula II, and the conventional processes suffer from drawbacks of critical generation of byproducts which affects further synthesis of Rosuvastatin.

According to one aspect of the present invention, nucleophilic substitution reaction for introduction of bromine with HBr or $PBr_3$ is not used but the compound of formula II is prepared by converting a compound of formula I by bromination into the compound of formula II as presented on the following scheme:

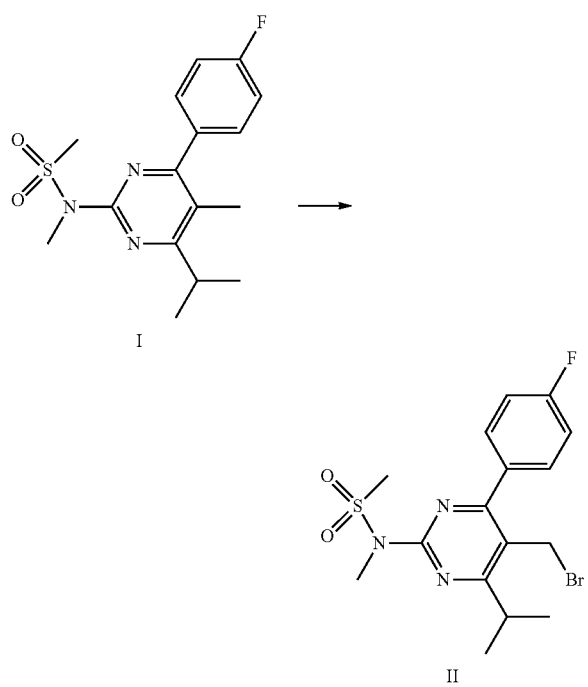

I

II

Since the compound of the formula I (N-(4-(4-fluorophenyl)-5-methyl-6-isopropylpyrimidin-2-yl)-N-methyl-methanesulfonamide) is used as the starting material, compound II (N-(4-(4-fluorophenyl)-5-(bromomethyl)-6-isopropylpyrimidin-2-yl)-N-methylmethanesulfonamide) can be obtained in only one step by bromination. The reaction can be carried out most efficiently by radical bromination reaction, optionally assisted by UV irridation and/or use of radical formers.

The above described bromination, notably when proceeding with radical reaction, significantly differs from the introduction of bromine by means of a nucleophilic substitution reaction (e.g. wherein compound of the formula III is converted into compound of the formula II). A nucleophilic substitution reaction requires a leaving group such as for example —OH of the compound of the formula III. In contrast to that, the compound of the formula I does not require such a leaving group.

In the above described bromination reaction of the present invention bromination agents such as N-bromoamides are preferably used. Advantageously, N-bromoamides provide for a constant, low concentration of bromine in the reaction mixture during reaction. More preferably, said N-bromoamides are selected from the group consisting of N-bromoacetamide, N,N-dibromobenzene sulfonamides; the N-bromoimides, such as N-bromosuccinimide, N-bromophthalimide, N-bromoglutarimide, 3-bromo-hydantoin, and 1,3-dibromo-5,5-dimethylhydantoin. N-bromosuccinimide is the most preferred brominating agent, since it is readily commercially availably and economically priced. Advantageously, the aforementioned bromination agents provide for mild reaction conditions resulting in less byproducts. HBr and PBr$_3$, which are aggressive and difficult to handle reactants which would negatively affect purity and yield of the compound of formula II, can be avoided.

The initial amount of said brominating agents is from about 0.1 to about 3 times the molar stoichiometric amount based on compound I, preferably about 0.9 to about 2.5 times, more preferably about 1.4 to about 2.2 times, and in particular about 2 times. In this way, efficient bromination resulting in high yields of compound II is provided, while economical amounts of brominating agent are used.

The above mentioned bromination reaction is suitably performed in organic solvent, preferably selected from the group consisting of acetone, ethyl acetate, hydrocarbons, aromatic hydrocarbons and acetonitrile. Most preferably, acetonitrile is used as organic solvent. The aforementioned organic solvents provide for suitable solubilisation of the reactants and advantageous reaction rates. Furthermore, these organic solvents are largely less toxic than carbon tetrachloride or chlorobenzene, which have been typically used in radical bromination of hydrocarbon side chains of aromatic substrates.

Preferably, the step of reacting a compound of formula I with brominating agent to give the compound of formula II is performed under a treatment of ultraviolet radiation, wherein said ultraviolet radiation has preferably a wavelength of about 200 to 400 nm, more preferably about 310 nm. Said ultraviolet radiation is preferably performed for 2 to 10 hours, more preferably for about 4 hours.

In a particular preferred embodiment of the invention, the bromination reaction is carried out at suitable temperature, preferably at a temperature between 0 to 90° C., more preferably between 10 to 65° C., even more preferably between 15 to 35° C. and in particular at an ambient temperature between 19 to 25° C. In this way, beneficial mild reaction conditions can be set, which further contributes to form less byproducts compared to a nuclephilic substitution reaction for introducing bromine wherein elevated reaction temperatures are used. Higher yields are obtained, purification will be facilitated, and further synthesis steps to obtain Rosuvastatin are less affected by critical byproducts.

Surprisingly, when using compound of formula I as starting compound, the above described radical bromination proceeds within relatively short reaction times and high yields, even if no radical former is applied. The absence of a radical former is advantageous, since the reaction becomes more safe in view of operational safety, because radical formers are quite reactive and therefore dangerous to handle compounds. Furthermore, the costs for a radical former can be saved. Therefore, it is preferred to perform the bromination without a radical former. In addition, significantly less impurities are formed during the reaction if no radical former is used.

Nevertheless, if one wishes to further accelerate the bromination reaction, a radical former may be applied. If used, the radical former is preferably an organic peroxide, an organic peracid, an organic hydroperoxide or an organic azo compound. These radical performers are suitable for accelerating/supporting radical reactions. More preferably, the radical former is selected from benzoyl peroxide or azoisobutyronitrile, since these radical performers are readily commercially available and inexpensive.

If a radical former is applied in the bromination reaction, the initial amount of radical former is between about 0 to 0.5 molar stoichiometric amount based on compound I, preferably about 0 to 0.07 molar stoichiometric amount based on compound I, and more preferably no radical former is applied. The aforementioned amounts of radical former provide for an advantageous acceleration of the reaction, while still providing a stable and safe reaction.

According to one embodiment, the compound of formula II is isolated and purified, preferably by crystallization. In this way, a simple and effective purification method is applied, compared to labor, time and material intensive column chromatography. Since the bromination reaction is performed under mild conditions, there are less byproducts, and therefore, crystallisation will be sufficient in order to provide an advantageously pure product. Furthermore, it was found by that crystallisation performed with an MTBE/hexane mixture, and in particular with an MTBE/hexane mixture wherein the volume ratio of MTBE to hexane is 2 to 1, preferably 1 to 1 and more preferably 2 to 3 is particularly advantageous.

The compound of formula I can be obtained by a targeted synthesis. Or, according to a preferred embodiment, the compound of formula I is obtained as a side product in the preparation of rosuvastatin intermediates where the compound of formula I is formed in a Wittig reaction between a phosphonium salt, phosphine oxide or phosphonate (compound of formula X) of a corresponding rosuvastatin heterocycle—or their converted reagents in the corresponding ylide or phosphorane form (for phosphonium salt) or corresponding carbanion (for phosphine oxide or phosphonate) (compound of formula X')—and a chiral statin side chain. An illustrative reaction system can be depicted from Scheme 1 below.

In Scheme 1, Z in the compound of formula X and X' is selected from the group consisting of phosphonium salt moiety, phosphine oxide moiety or phosphonate moiety:

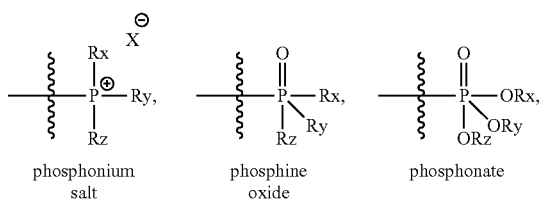

phosphonium salt     phosphine oxide     phosphonate wherein Rx, Ry, Rz are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, preferably phenyl, and $X^\ominus$ is an anion, preferably a halogen or carboxylate anion, more preferably chloride, bromide or trifluoroacetate;

Further in Scheme 1, $P_1$ and $P_2$ independently denote conventional hydroxyl protecting groups. The protecting group $P_1$ and $P_2$ may be any conventionally used protecting group for hydroxyl groups, for example selected independently from the group consisting of alkyl, branched alkyl, acyl, silyl or similar group, more particularly selected from acetonide, acetyl (Ac), pivaloyl (Piv), p-toluenesulfonyl (TOS), β-methoxyethoxymethyl ether (MEM), methoxymethyl ether (MOM), p-methoxybenzyl ether (PMB), methylthiomethyl ether, t-butyl, tetrahydropyranyl (THP), benzyl (Bn), diphenylmethyl or triphenylmethyl group, preferably silyl protecting group which can be represented by a formula $SiR_1'R_2'R_3'$ in which $R_1'$, $R_2'$, $R_3'$ are independently selected from alkyl (preferably $C_1$-$C_6$) or aryl (preferably $C_5$-$C_{10}$), such as $SiMe_3$ (TMS), $SiMe_2{}^tBu$ (TBDMS), $Si(i\text{-}Pr)_3$ (TIPS), $SiPh_2{}^tBu$, $SiMe_2Ph$.

Hence, as illustrated in Scheme 1, the protected final rosuvastatin intermediate can be used to proceed with the final synthesis steps for obtaining rosuvastatin or its salts, while alternatively or in addition the compound of formula I can be utilized by being recycled into another (same or different) rosuvastatin synthesis route.

Prior to the respective further use, the reaction products obtained in the Wittig reaction can be respectively separated by appropriate and known methods into the compound of formula I and the compound selected from formulas XI or XI'.

Scheme 1

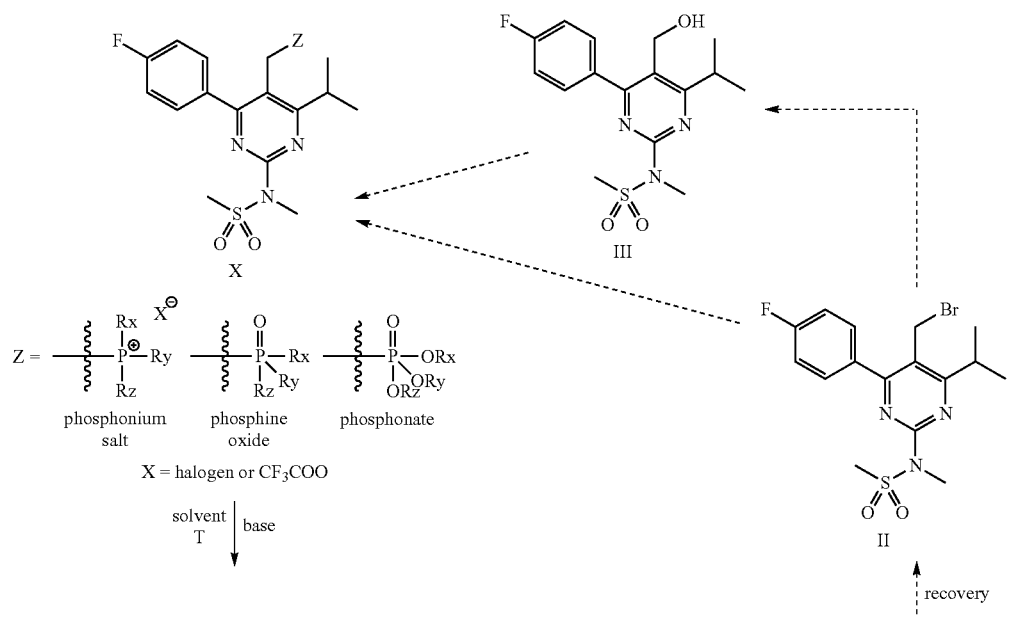

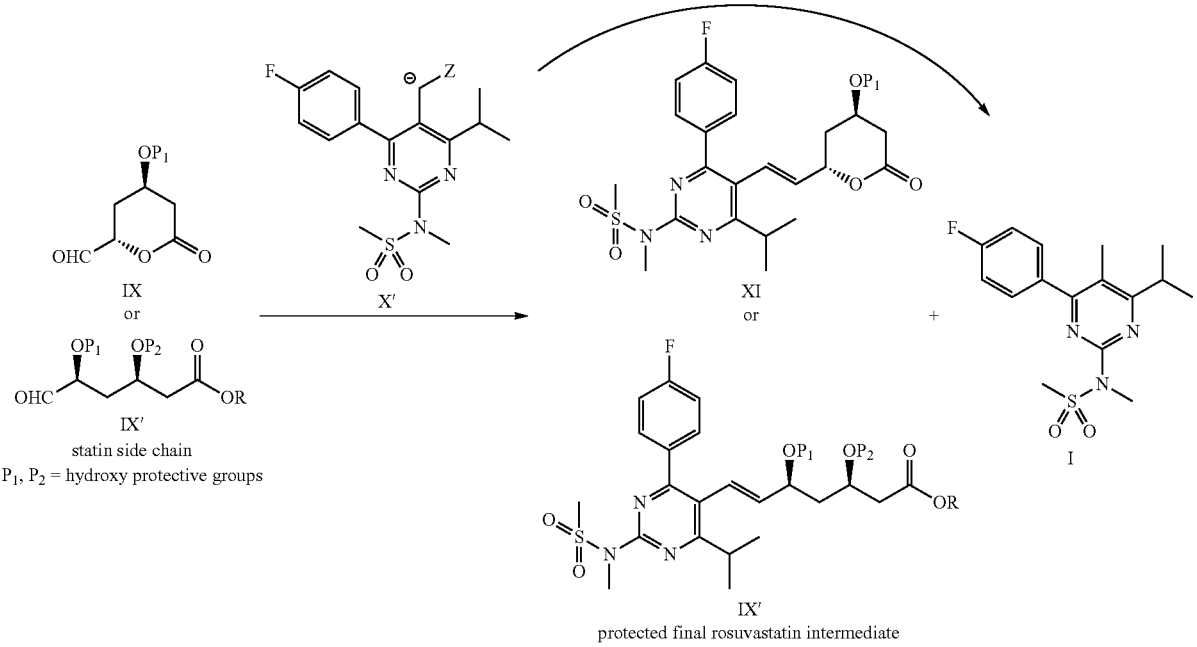

statin side chain
P₁, P₂ = hydroxy protective groups

Scheme 1

Advantageously and surprisingly, the compound of formula I is more substantially formed when the Wittig reaction is performed with excess of the phosphonium salt (or its ylide or phosphorane), phosphine oxide (or its carbanion) or phosphonate (or its carbanion) Wittig reagent (e.g. a molar excess of compound X or X' over compound IX or IX' of suitably 5% or more, preferably 10% or more, and particularly 15% or more), more effectively after quenching with protic solvent, and/or when the Wittig reaction is performed in the presence of water or other protic molecules such as alcohols (e.g. methanol, ethanol, propanol, isopropanol butanol and phenols), etc. The presence of water or other protic molecules may be accomplished by addition of water or typically known protic solvent types such as alcohols, but alternatively it is preferred and sufficient if e.g. undried or wet, or insufficiently dried solvent(s) introduced into the Wittig reaction is (are) used. According to another efficient embodiment, the starting compound of formula IX can obtained from its hydrate form in an appropriate solvent but without removal of the released water molecules, as shown in the following reaction scheme,

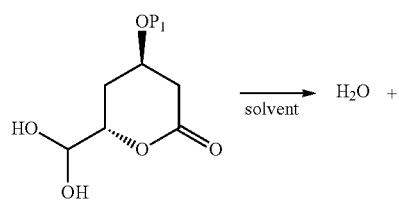

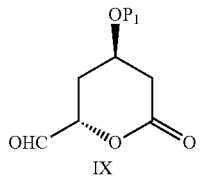

and is then directly (i.e. without removal of water) introduced into the Wittig reaction. An appropriate solvent for the following reaction is tetrahydrofuran (THF), for example.

The provision and the utilization of the compound of formula I has a significant favorable impact on the efficiency of the overall process of the rosuvastatin synthesis. Since the heterocyclic part of the molecule is prepared in many laborious synthetic steps as disclosed e.g. in EP 521471, it is highly advantageous to recover the valuable compound of formula I and render it utilizable by specifically converting it into compounds of formula II or III, which in turn are capable of being beneficially used further, for example by converting them again into a phosphonium salt, phosphine oxide or phosphonate representing a further starting material for the preparation of rosuvastatin intermediates via Wittig reaction (as exemplified for example in Scheme 1 above). The compound of formula II can be directly transformed to phosphonium salt derivative, phosphine oxide or phosphonate (see e.g. US2005/0124639). Alternatively, the compound of formula I can be transformed to the compound of formula III, which can be converted to phosphonium salt derivative, phosphine oxide or phosphonate (see e.g. WO2007/017117). Although the compound of formula II can be prepared by prior art processes (see e.g. WO2007/017117), this process cannot be applied for the recovery of compound I to phosphonium salt derivative, phosphine oxide or phosphonate. Similarly, prior-art processes for the preparation of compound III as disclosed in the EP521471 cannot be used for recovery of the compound of formula I to phosphonium salt derivative, phosphine oxide or phosphonate.

Therefore, the provision of compound of formula I, besides being useful of its own, can contribute to a markedly improved overall yield of a rosuvastatin synthesis.

According to another aspect of the invention, a compound of formula III is prepared by a process comprising the step of converting a compound of formula II by hydrolysis into the compound of formula III, as depicted in the following scheme:

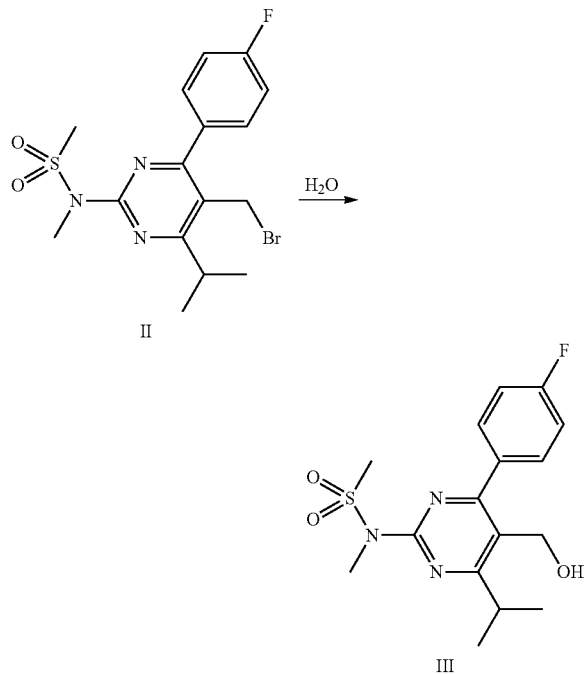

According to a preferred embodiment, the above mentioned conversion is performed in the presence of an inorganic base, preferably an alkaline or alkaline earth carbonate or hydrogencarbonate, more preferably NaHCO$_3$ is used as the inorganic base. Besides, it is preferred to add said inorganic base to the reaction mixture in the form of a saturated aqueous solution.

Preferably, the initial amount of inorganic base is between about 1 to 10 times the molar stoichiometric amount based on compound II, preferably about 3 to 7 times and more preferably 5 to 6 times.

According to another aspect of the present invention, the compound of formula III is prepared by a one-pot synthesis converting compound of formula I via non-isolated compound of formula II into the compound of formula III as depicted in the following scheme.

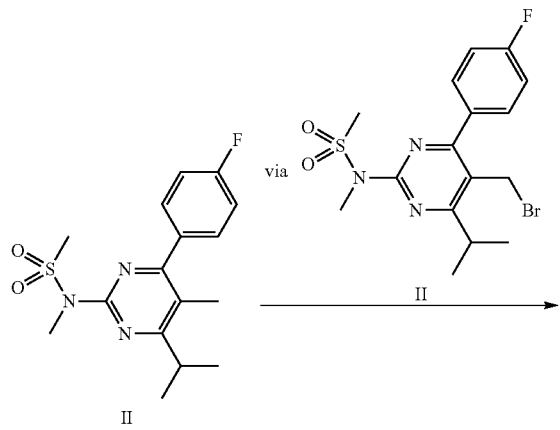

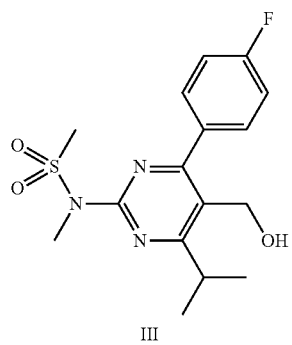

It was found feasible to yield compound of formula III without isolating and purifying the intermediate compound of formula II. Therefore, the number of process steps can be reduced, which makes the whole synthesis route substantially more efficient.

Preferably, the aforementioned one-pot synthesis is carried out by converting compound of formula I into compound of formula II by the above described bromination according to the present invention, or/and converting compound of formula II into compound of formula III by the above described hydrolysis according to the invention.

Furthermore, it is preferred to add a solvent to the resulting reaction batch after conversion of compound of formula I into compound of formula II is performed, in order to dilute the reaction batch. Conversion of compound of formula I into compound of formula II may e.g. be monitored by thin layer chromatography or high pressure liquid chromatography (HPLC). Preferably, said solvent for dilution is selected from the group of solvents described for the above mentioned bromination reaction, and more preferably it is the same solvent as used in the bromination reaction. Thereby, an advantageous degree of dissolution of the compound of the formula II is obtained, which in turn provides for a smooth hydrolysis giving rise to high yields.

According to a further embodiment, the process for preparing the compound of the formula III further comprises the step of purifying compound of formula III, preferably by crystallization. In this way, a simple and effective purification method is applied, compared to labor, time and material intensive column chromatography. Since the hydrolysis reaction provides for a full conversion of compound of the formula II into compound of the formula III, crystallisation will be sufficient in order to provide an advantageously pure product. Furthermore, it was found by that crystallisation performed with an MTBE/hexane mixture, and in particular with an MTBE/hexane mixture wherein the volume ratio of MTBE to hexane is 2 to 1, preferably 1 to 1 and more preferably 2 to 3 is particularly advantageous.

The key intermediate compounds of formula II and III can then be subjected to further synthesis steps in order to yield Rosuvastatin or pharmaceutically acceptable salts thereof by synthesis routes known to or readily devisable by a person skilled in the art. As shown in the scheme below, following synthesis routes may be applied:

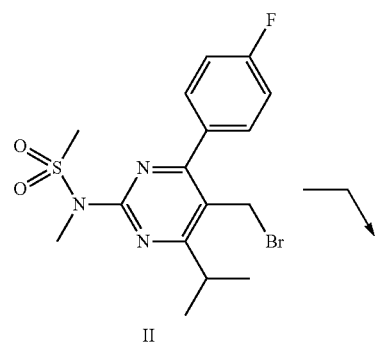
II
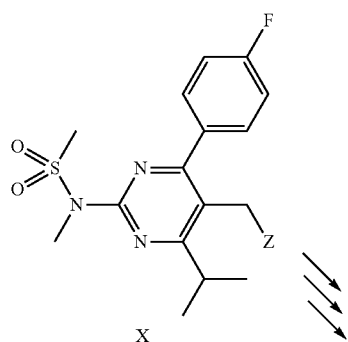
X
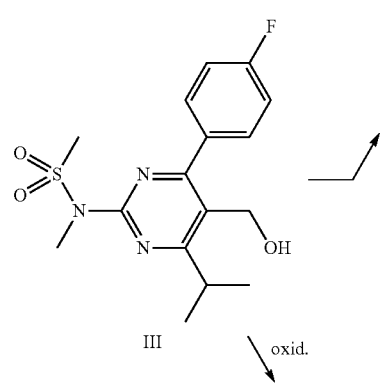
III
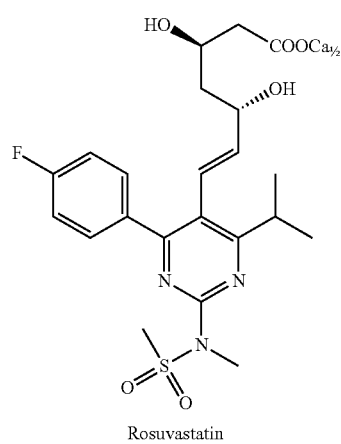
Rosuvastatin
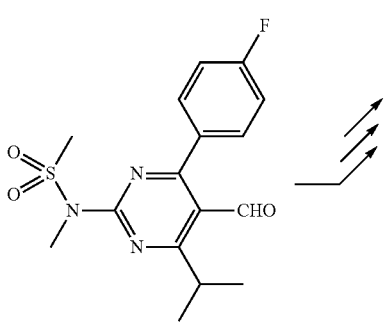
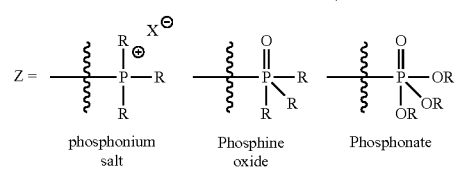
Z = phosphonium salt, Phosphine oxide, Phosphonate For preparing a pharmaceutical composition comprising Rosuvastatin or pharmaceutically acceptable salts thereof as active ingredient, first Rosuvastatin or pharmaceutically acceptable salts thereof is provided by the process as described above.

Then, the thus prepared Rosuvastatin or pharmaceutically acceptable salts thereof is suitably admixed with at least one suitable pharmaceutically acceptable excipient. Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology.

Preferably, excipients may be selected from the group consisting of lactose, microcrystalline cellulose, cellulose derivatives, e.g. hydroxypropylcellulose, polyacrylates, calcium carbonate, starch, colloidal silicone dioxide, sodium starch glycolate, talc, magnesium stearate, polyvinylpyrrolidone, polyethylene glycol and other excipients known in the field of the pharmaceutical technology.

Experimental Procedures

Example 1

Preparation of N-(4-(4-fluorophenyl)-6-isopropyl-5-methylpyrimidin-2-yl)-N-methylmethanesulfonamide (I)

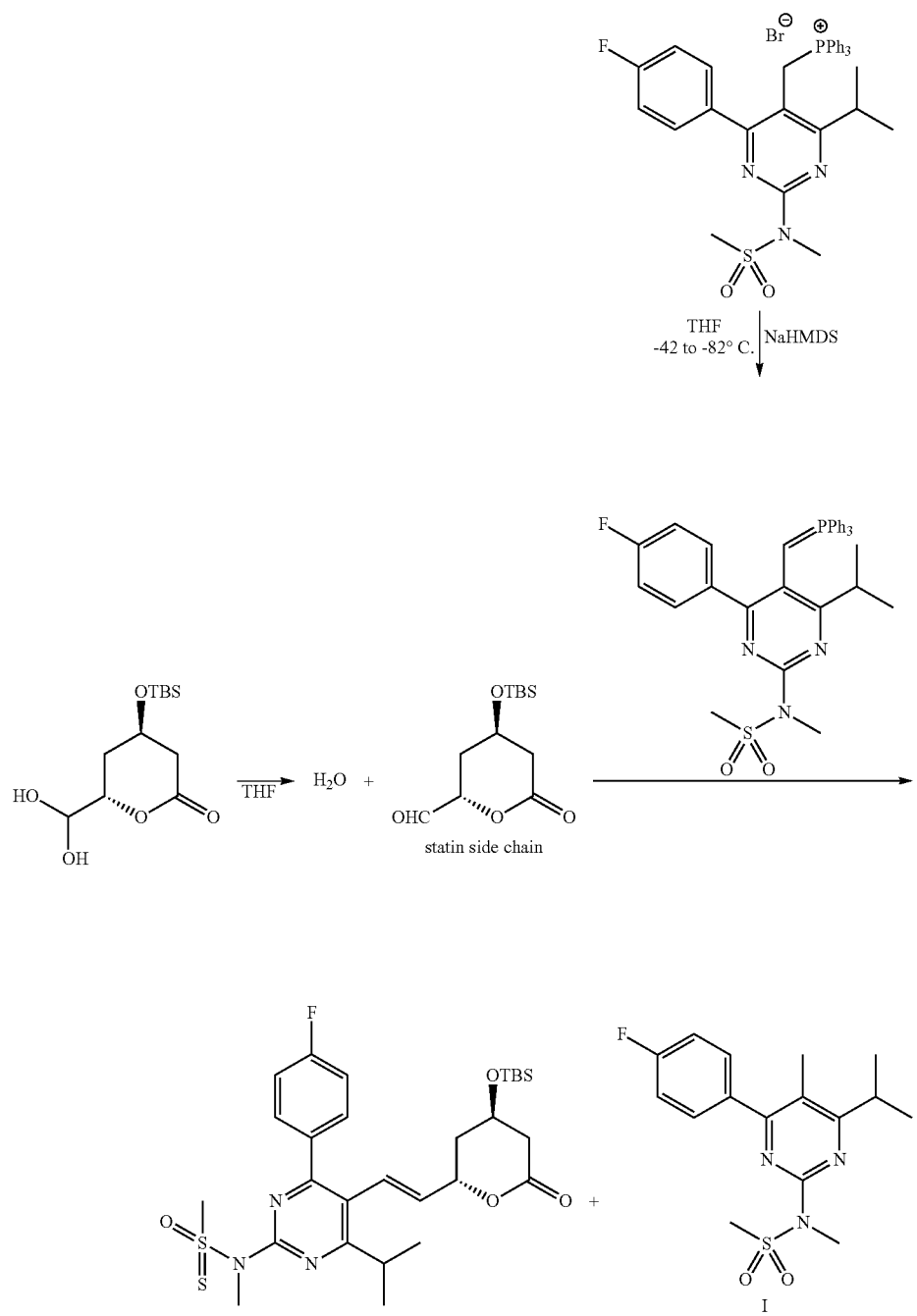

To a cold (−42° C.), stirred suspension of ((4-(4-fluorophenyl)-6-isopropyl-2-(N-methylmethylsulfonamido)pyrimidin-5-yl)methyl)triphenylphosphonium bromide (814 mg, 1.20 mmol) in tetrahydrofuran (25 mL) is added sodium hexamethyldisilazane in THF (1.2 mL of 1.0 M, 1.20 mmol). The reaction mixture is stirred for 45 min at −42° C., cooled to −82° C., and treated with a solution of (2S,4R)-4-(tert-butyldimethylsilyloxy)-6-oxo-tetrahydro-2H-pyran-2-carbaldehyde (266 mg, 1.03 mmol) obtained by dissolution of its hydrate (284 mg, 1.03 mmol) in 15 mL of tetrahydrofurane without removal of released water. After 30 min of stirring, the solution is warmed to −53 to −58° C. and stirred further for 6 hours. Then, the mixture is allowed to warm to ambient temperature in 100 min and treated with saturated ammonium chloride solution (40 mL). After stirring for 10 min at 10° C. the aqueous phase is treated with 20 mL of water and 40 mL of saturated solution of brine. The product is extracted with t-BuMeO (50 mL+4×30 mL). The combined organic layers dried (MgSO$_4$) and concentrated under reduced pressure (11 mbar) at 40° C. to give white solid. The residue is purified by silica gel chromatography (elution with hexane/AcOEt=3:1 mixture) to give 170 mg (42%) of N-(4-(4-fluorophenyl)-6-isopropyl-5-methylpyrimidin-2-yl)-N-methylmethanesulfonamide (I). R$_f$ (hexane/AcOEt=3:1)=0.42. White solid m.p. 113-114° C. $^1$H NMR (300 MHz, CDCl$_3$, 25° C.): δ=7.56 (m, 2H), 7.14 (m, 2H), 3.55 (s, 3H), 3.51 (s, 3H), 3.31 (sept, $^3$J=6.7 Hz, 1H), 2.28 (s, 3H), 1.30 (d, $^3$J=6.7 Hz, 6H) ppm. $^{13}$C NMR (75 MHz, CDCl$_3$, 25° C.): δ=175.3, 164.6, 163.8 (d, J$_{C-F}$=249 Hz), 156.7, 134.7 (d, J$_{C-F}$=3.4 Hz), 131.1 (d, J$_{C-F}$=8.3 Hz), 118.6, 115.1 (d, J$_{C-F}$=21.5 Hz), 42.2, 33.0, 31.8, 21.2, 14.1 ppm. MS (ESI+) m/z (%): 338 (MH$^+$, 100). Anal. Calcd for C$_{16}$H$_{20}$FN$_3$O$_2$S: C, 56.95; H, 5.97; N, 12.45. Found: C, 56.95; H, 5.85; N, 12.45.

Example 2

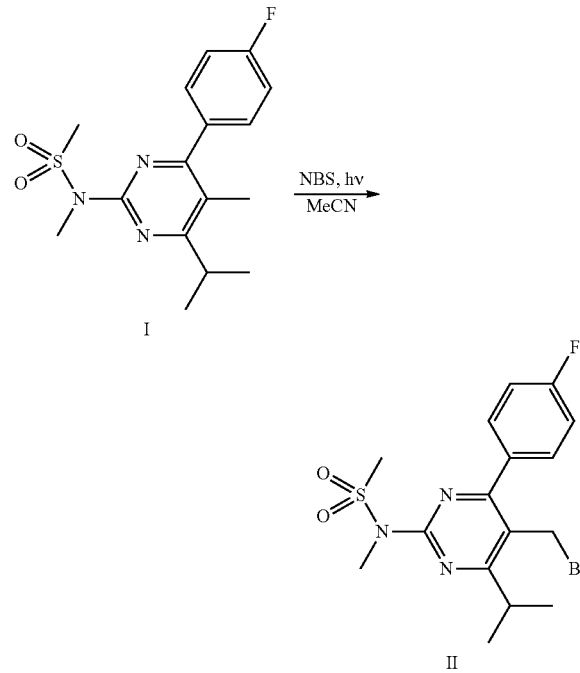

N-(4-(4-fluorophenyl)-5-methyl-6-isopropylpyrimidin-2-yl)-N-methylmethanesulfonamide (112.5 mg, 0.33 mmol, 1 equiv.) and N-bromosuccinimide (NBS) (126 mg, 0.72 mmol, 2.1 equiv.) were dissolved in 2 mL of acetonitrile. The mixture was irradiated with light of a wavelength A=310 nm for 4 hours at ambient temperature (about 20° C.). Then, water (10 mL) was added and the mixture was extracted with CH$_2$Cl$_2$ (3×10 mL). The combined organic phases were washed with 10 mL of brine, and the obtained solution was dried with Na$_2$SO$_4$. Solvent was removed under the reduced pressure to give 138.6 mg of crude N-(4-(4-fluorophenyl)-5-(bromomethyl)-6-isopropylpyrimidin-2-yl)-N-methylmethanesulfonamide (II), which contained 93% of N-(4-(4-fluorophenyl)-5-(bromomethyl)-6-isopropylpyrimidin-2-yl)-N-methylmethanesulfonamide (II) as determined by $^1$H-NMR integral. This product can be further purified by crystallization from MTBE/hexane mixture to afford pure material.

Example 3

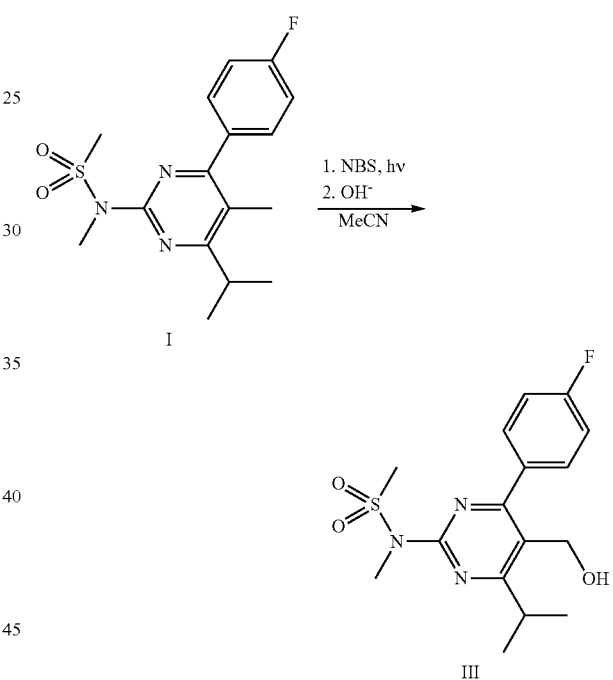

N-(4-(4-fluorophenyl)-5-methyl-6-isopropylpyrimidin-2-yl)-N-methylmethanesulfonamide (112.5 mg, 0.33 mmol, 1 equiv.) and N-bromosuccinimide (NBS) (118.7 mg, 0.66 mmol, 2 equiv.) were dissolved in 2 mL of acetonitrile. The mixture was irradiated with light of a wavelength A=310 nm for 4 hours at ambient temperature (about 20° C.). The obtained yellow solution was diluted with 1 mL of acetonitrile. After 2 mL of saturated NaHCO$_3$ solution was added, the obtained mixture was further stirred under reflux for 4 hours. Then the mixture was cooled to room temperature, water (10 mL) was added and the mixture was extracted with CH$_2$Cl$_2$ (3×10 mL). The combined organic phases were washed with 10 mL of brine, and the obtained solution was dried with Na$_2$SO$_4$. Solvent was removed under the reduced pressure to give 110.8 mg (95%) of crude N-(4-(4-fluorophenyl)-5-(hydroxymethyl)-6-isopropylpyrimidin-2-yl)-N-methylmethanesulfonamide (III) which contained 77% of N-(4-(4-fluorophenyl)-5-(hydroxymethyl)-6-isopropylpyrimidin-2-yl)-N-methylmethanesulfonamide (III) as determined by $^1$H-NMR integral. This product can be further purified by crystallization from MTBE/hexane mixture to afford pure material (HPLC area %=99.6) with $T_m$=140-141° C.

The invention claimed is:

1. A process for preparing rosuvastatin, comprising:

(a) reacting a compound of formula IX or IX'

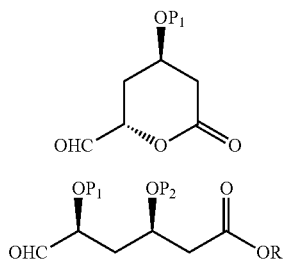

wherein $P_1$ and $P_2$ respectively denote same or different hydroxy protecting groups and R is selected from alkyl or aryl;

with a compound of formula X or X'

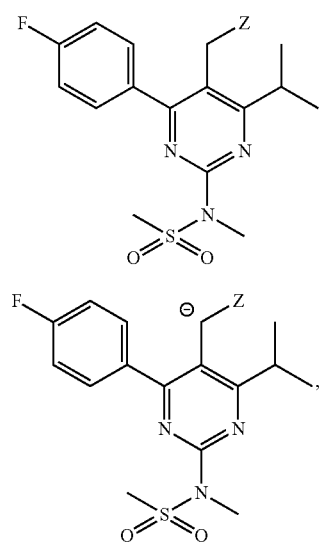

wherein Z is selected from the group consisting of:

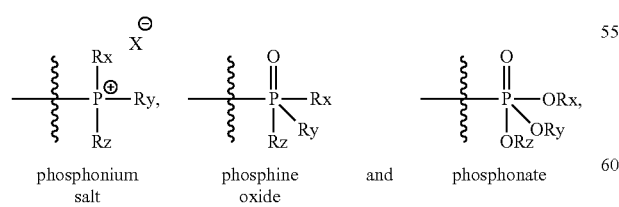

and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl and $X^\ominus$ is an anion;

(b) obtaining reaction products of a compound of formula I

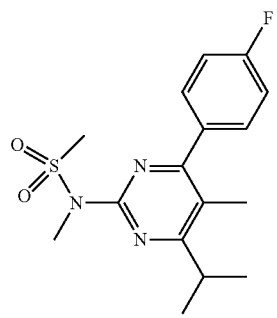

and a compound selected from formulas XI or XI'

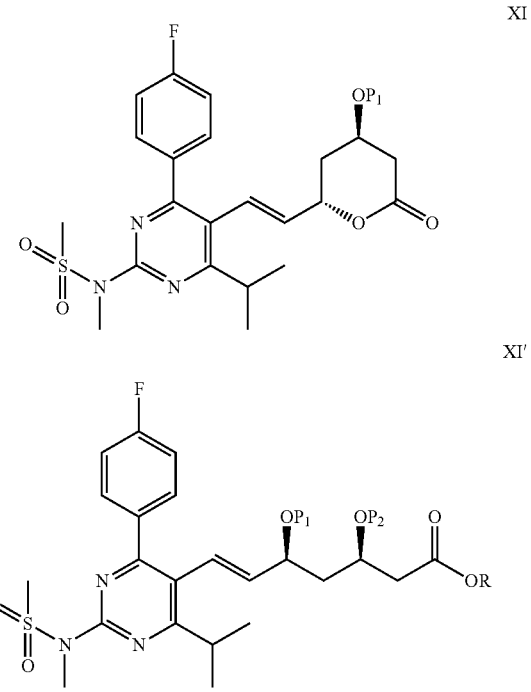

wherein $P_1$ and $P_2$ are as defined above;

(c) separating the obtained reaction products into the compound of formula I and the compound selected from formulas XI or XI'; and (d) using the obtained compound selected from formulas XI or XI' for conversion into rosuvastatin or pharmaceutically acceptable salts thereof, wherein the compound of formula I obtained in step (c) is used in a recycling process for producing rosuvastatin comprising:

(e) converting the compound of formula I into the compound of formula II by bromination wherein said bromination is performed with an N-bromoamide as a brominating agent and optionally converting the compound of formula II into the compound of formula III by hydrolysis (f) converting the compound of formula II or III, respectively, to the compound of formula XI or XI'; and (g) subjecting the compounds of formula XI or XI' obtained by converting the compounds of formula II or III, respectively, to further synthesis steps to yield rosuvastatin or pharmaceutically acceptable salts thereof.

2. The method of claim 1, wherein Rx, Ry, and Rz are each phenyl.

3. The method of claim 2, wherein $X^{\ominus}$ is selected from the group consisting of chloride, bromide, and trifluoroacetate.

4. The process according to claim 1, wherein said N-bromoamide is selected from the group consisting of N-bromoacetamide, N,N-dibromobenzene sulfonamides, N-bromosuccinimide, N-bromophthalimide, N-bromoglutarimide, 3-bromo-hydantoin and 1,3-dibromo-5,5-dimethylhydantoin.

5. The process according to claim 1, wherein the initial amount of brominating agent is from about 1 to about 3 times the molar stoichiometric amount based on compound I.

6. The process according to claim 1, wherein the initial amount of brominating agent is from about 1.2 to about 2.5 times the molar stoichiometric amount based on compound I.

7. The process according to claim 1, wherein the initial amount of brominating agent is about 2 times the molar stoichiometric amount based on compound I.

8. The process according to claim 1, comprising:
(a) reacting a compound of formula IX or IX' wherein $P_1$ and $P_2$ respectively denote same or different hydroxy protecting groups and R is selected from alkyl or aryl;

with a compound of formula X or X' wherein Z is selected from the group consisting of:

phosphonium salt     phosphine oxide     and     phosphonate and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl and $X^{\ominus}$ is an anion;

(b) obtaining reaction products of
a compound of formula I

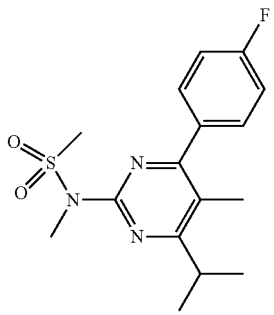

I and
a compound selected from formulas XI or XI'

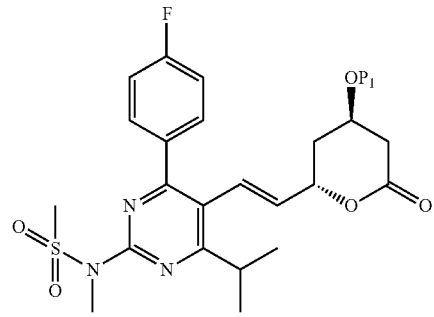

XI

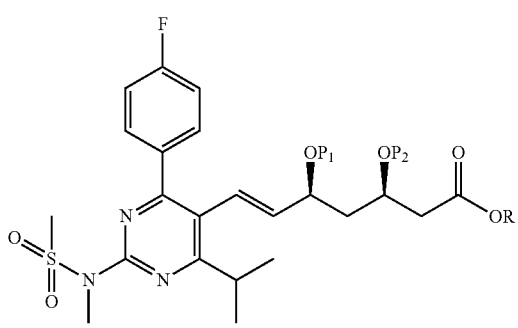

XI' wherein $P_1$ and $P_2$ are as defined above;
(c) separating the obtained reaction products into the compound of formula I and the compound selected from formulas XI or XI'; and
(d) using the obtained compound selected from formulas XI or XI' for conversion into rosuvastatin or pharmaceutically acceptable salts thereof,
wherein the compound of formula I obtained in step (c) is used in a recycling process for producing rosuvastatin comprising:
(e) converting the compound of formula I into the compound of formula II by bromination, wherein the bromination reaction is performed in an organic solvent selected from the group consisting of acetone, ethyl acetate, hydrocarbons, aromatic hydrocarbons, acetonitrile, and mixtures thereof

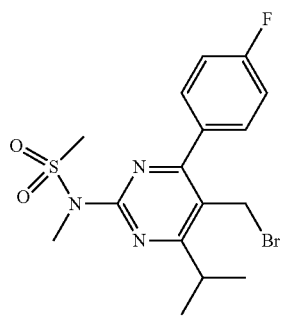

II and optionally converting the compound of formula II into the compound of formula III by hydrolysis

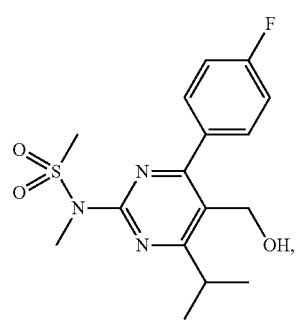

III (f) converting the compound of formula II or III, respectively, to the compound of formula XI or XI'; and
(g) subjecting the compounds of formula XI or XI' obtained by converting the compounds of formula II or III, respectively, to further synthesis steps to yield rosuvastatin or pharmaceutically acceptable salts thereof.

9. The process according claim 8, wherein the bromination reaction of step e) is performed in acetonitrile.

10. The process according to claim 1, comprising:
(a) reacting a compound of formula IX or IX'

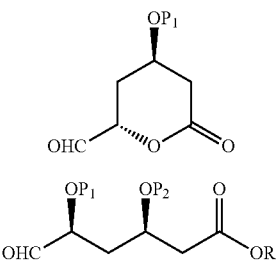

IX

IX' wherein $P_1$ and $P_2$ respectively denote same or different hydroxy protecting groups and R is selected from alkyl or aryl;

with a compound of formula X or X'

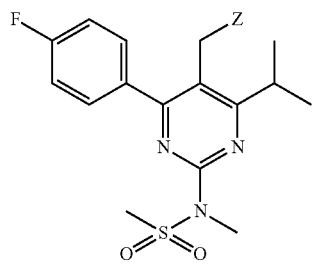

X

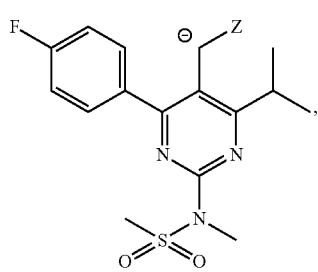

X' wherein Z is selected from the group consisting of:

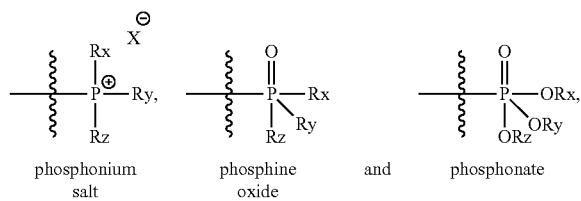

phosphonium salt     phosphine oxide     and     phosphonate and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl and $X^{\ominus}$ is an anion;

(b) obtaining reaction products of
a compound of formula I

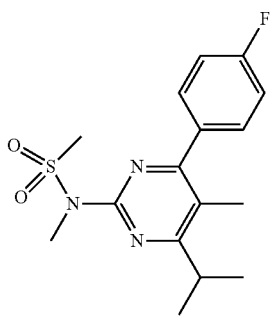

I and
a compound selected from formulas XI or XI'

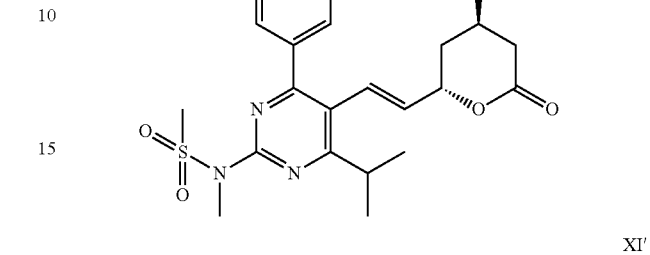

XI

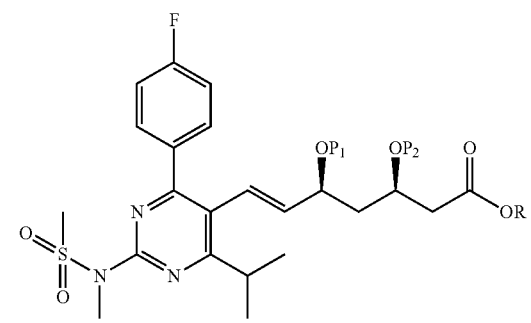

XI' wherein $P_1$ and $P_2$ are as defined above;

(c) separating the obtained reaction products into the compound of formula I and the compound selected from formulas XI or XI'; and (d) using the obtained compound selected from formulas XI or XI' for conversion into rosuvastatin or pharmaceutically acceptable salts thereof, wherein the compound of formula I obtained in step (c) is used in a recycling process for producing rosuvastatin comprising:

(e) converting the compound of formula I into the compound of formula II by bromination wherein the bromination reaction is performed without HBr or $PBr_3$ as a brominating agent

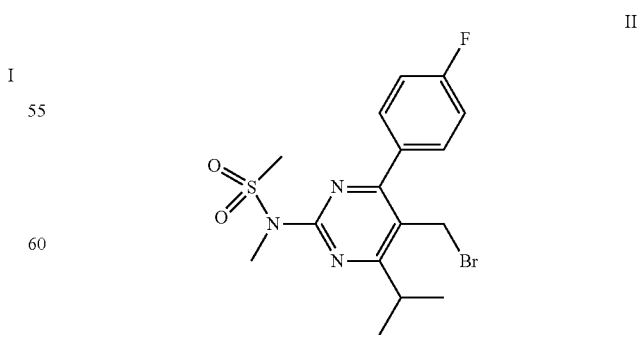

II and optionally converting the compound of formula II into the compound of formula III by hydrolysis

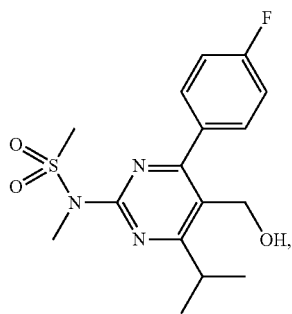
III (f) converting the compound of formula II or III, respectively, to the compound of formula XI or XI'; and
(g) subjecting the compounds of formula XI or XI' obtained by converting the compounds of formula II or III, respectively, to further synthesis steps to yield rosuvastatin or pharmaceutically acceptable salts thereof.

11. The process according to claim 1, comprising:
(a) reacting a compound of formula IX or IX'

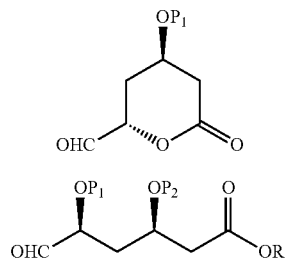

IX

IX' wherein $P_1$ and $P_2$ respectively denote same or different hydroxy protecting groups and R is selected from alkyl or aryl;
with a compound of formula X or X'

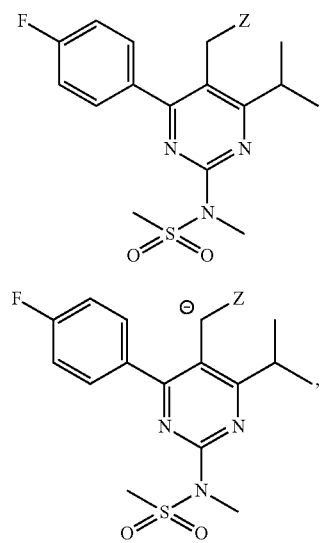

X

X' wherein Z is selected from the group consisting of:

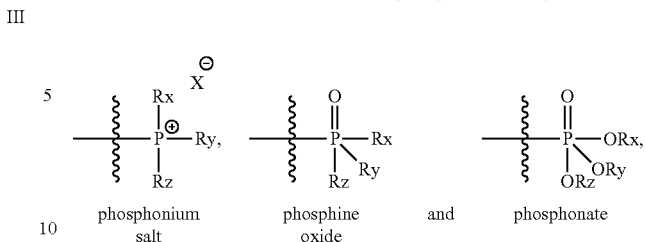

phosphonium salt    phosphine oxide    and    phosphonate and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_5$ cycloalkenyl or aryl and $X^\ominus$ is an anion;
(b) obtaining reaction products of
a compound of formula I

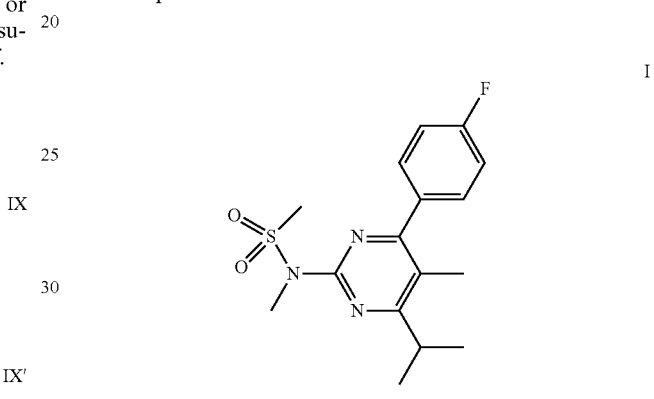

I and
a compound selected from formulas XI or XI'

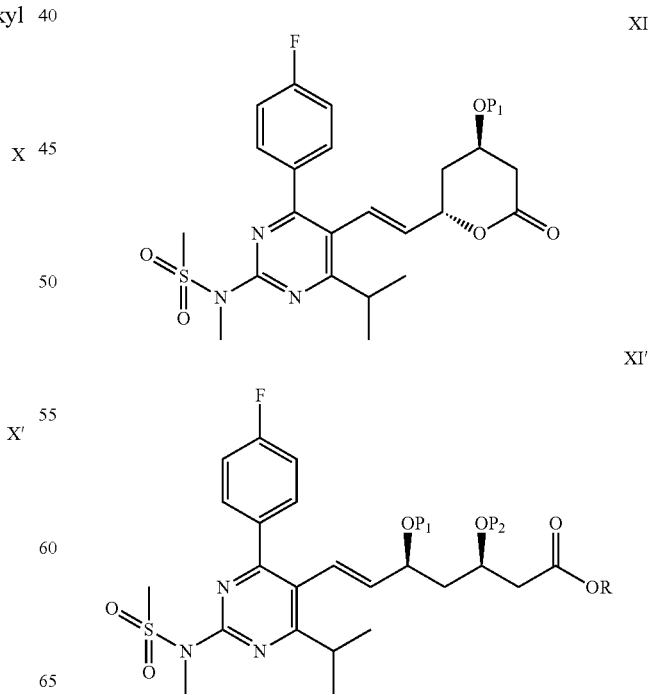

XI

XI' wherein $P_1$ and $P_2$ are as defined above;
(c) separating the obtained reaction products into the compound of formula I and the compound selected from formulas XI or XI'; and
(d) using the obtained compound selected from formulas XI or XI' for conversion into rosuvastatin or pharmaceutically acceptable salts thereof,
wherein the compound of formula I obtained in step (c) is used in a recycling process for producing rosuvastatin comprising:
(e) converting the compound of formula I into the compound of formula II by bromination, wherein the bromination reaction is performed under treatment of ultraviolet radiation, wherein said ultraviolet radiation has a wavelength of about 200 to 400 nm

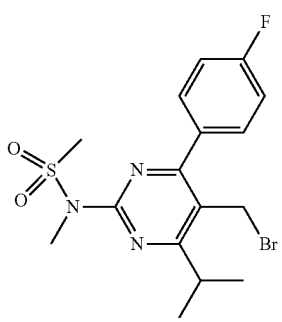

II and optionally converting the compound of formula II into the compound of formula III by hydrolysis

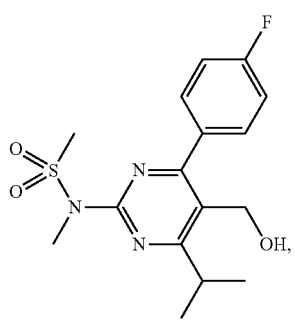

III (f) converting the compound of formula II or III, respectively, to the compound of formula XI or XI'; and
(g) subjecting the compounds of formula XI or XI' obtained by converting the compounds of formula II or III, respectively, to further synthesis steps to yield rosuvastatin or pharmaceutically acceptable salts thereof.

12. The process according to claim 1, comprising:
(a) reacting a compound of formula IX or IX'

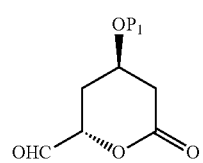

IX

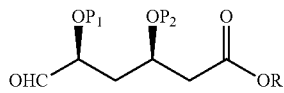

IX' wherein $P_1$ and $P_2$ respectively denote same or different hydroxy protecting groups and R is selected from alkyl or aryl;
with a compound of formula X or X'

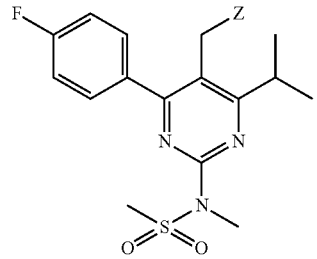

X

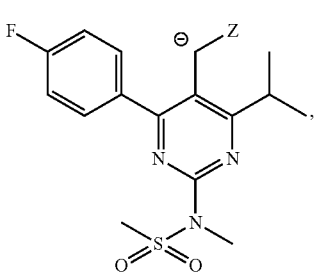

X' wherein Z is selected from the group consisting of:

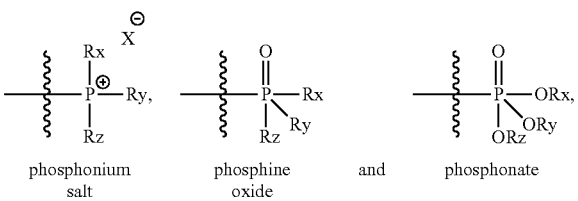

phosphonium salt    phosphine oxide    and    phosphonate and wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl and $X^{\ominus}$ is an anion;
(b) obtaining reaction products of
a compound of formula I

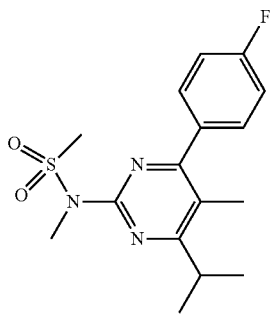

I and
a compound selected from formulas XI or XI'

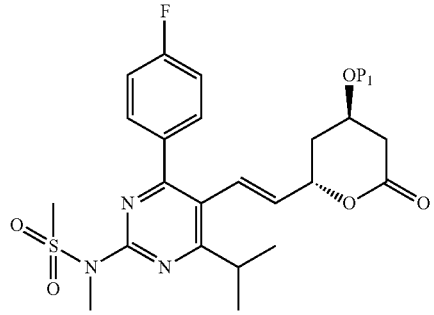

XI

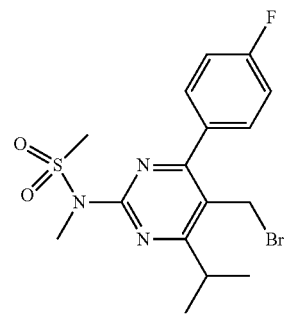

II and optionally converting the compound of formula II into the compound of formula III by hydrolysis

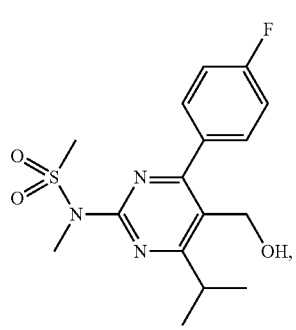

III

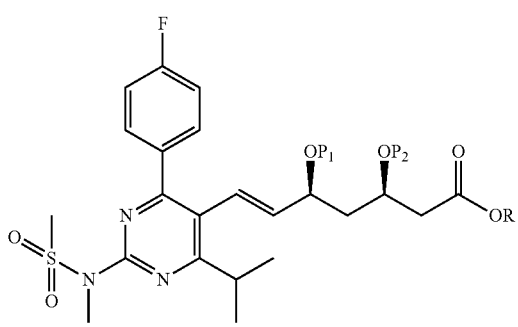

XI' wherein $P_1$ and $P_2$ are as defined above;

(c) separating the obtained reaction products into the compound of formula I and the compound selected from formulas XI or XI'; and (d) using the obtained compound selected from formulas XI or XI' for conversion into rosuvastatin or pharmaceutically acceptable salts thereof, wherein the compound of formula I obtained in step (c) is used in a recycling process for producing rosuvastatin comprising:

(e) converting the compound of formula I into the compound of formula II by bromination, wherein the bromination reaction of stop o) is carried out at a temperature from 0 to 90° C.

(f) converting the compound of formula II or III, respectively, to the compound of formula XI or XI'; and (g) subjecting the compounds of formula XI or XI' obtained by converting the compounds of formula II or III, respectively, to further synthesis steps to yield rosuvastatin or pharmaceutically acceptable salts thereof.

13. The process according claim 12, wherein the bromination reaction of step e) is carried out at a temperature from 15 to 35° C.

14. The process according claim 12, wherein the bromination reaction of step e) is carried out at a temperature from 19 to 25° C.

15. The process according to claim 1, further comprising a step of purifying the compound of formula II.

16. The process according to claim 1, wherein the compound of formula II is converted into the compound of formula III, and further comprising a step of purifying the compound of formula III.

17. The process according to claim 15, wherein the step of purifying comprises crystallization performed with an MTBE/hexane mixture.

18. The process according to claim 16, wherein the step of purifying comprises crystallization performed with an MTBE/hexane mixture.

\* \* \* \* \*